United States Patent [19]

Huetter et al.

[11] Patent Number: 5,456,903
[45] Date of Patent: Oct. 10, 1995

[54] METHOD OF MAKING A TARTAR CONTROL BAKING SODA DENTIFRICE

[75] Inventors: Thomas E. Huetter, West Chester; Donald J. White, Jr., Fairfield; Edward R. Cox, Germantown, all of Ohio; Cloyd Dixon, Jr., Covington, Ky.

[73] Assignee: Procter & Gamble, Cincinnati, Ohio

[21] Appl. No.: 365,975

[22] Filed: Dec. 28, 1994

Related U.S. Application Data

[63] Continuation of Ser. No. 279,305, Jul. 22, 1994, abandoned, which is a continuation of Ser. No. 52,324, Apr. 23, 1993, abandoned.

[51] Int. Cl.⁶ .................. A61K 7/16; A61K 7/18
[52] U.S. Cl. .................. 424/57; 424/49; 424/57
[58] Field of Search .......................... 424/49–57

[56] References Cited

U.S. PATENT DOCUMENTS

| | | | |
|---|---|---|---|
| 3,927,201 | 12/1975 | Baynes et al. | 424/57 |
| 3,927,202 | 12/1975 | Harvey et al. | 424/57 |
| 4,144,322 | 3/1979 | Cordon et al. | 424/49 |
| 4,487,757 | 12/1984 | Kiozpeoplou | 424/7.1 |
| 4,623,536 | 11/1986 | Winston et al. | 424/49 |
| 4,678,662 | 7/1987 | Chan | 424/57 |
| 4,684,518 | 7/1987 | Parran, Jr. et al. | 424/52 |
| 4,721,614 | 1/1988 | Winston et al. | 424/52 |
| 4,853,213 | 8/1989 | Thame | 424/58 |
| 4,891,211 | 1/1990 | Winston | 424/52 |
| 4,925,655 | 5/1990 | Smigel et al. | 424/52 |
| 4,978,521 | 12/1990 | Blue | 424/7.1 |
| 4,992,256 | 2/1991 | Skaggs et al. | 424/49 |
| 4,999,184 | 3/1991 | Parran, Jr. et al. | 424/52 |
| 5,037,633 | 8/1991 | Ziemkiewicz et al. | 424/49 |
| 5,037,634 | 8/1991 | Williams et al. | 424/49 |
| 5,089,254 | 2/1992 | Coulson | 424/52 |
| 5,145,666 | 9/1992 | Lukacovic et al. | 424/52 |
| 5,176,900 | 1/1993 | White et al. | 424/52 |
| 5,180,576 | 1/1993 | Winston et al. | 424/52 |
| 5,182,099 | 1/1993 | Jonsson et al. | 424/49 |
| 5,215,740 | 6/1993 | Domke et al. | 424/52 |
| 5,256,402 | 10/1993 | Prencipe et al. | 424/53 |
| 5,281,410 | 1/1994 | Lukacovic et al. | 424/52 |
| 5,294,432 | 3/1994 | Winston et al. | 424/52 |
| 5,318,773 | 6/1994 | Winston et al. | 424/52 |
| 5,376,360 | 12/1994 | Domke et al. | 424/52 |

FOREIGN PATENT DOCUMENTS

| | | | |
|---|---|---|---|
| 2188548 | 4/1987 | United Kingdom | A61K 7/18 |

*Primary Examiner*—Shep K. Rose
*Attorney, Agent, or Firm*—Kim William Zerby; Douglas C. Mohl; Jacobus C. Rasser

[57] ABSTRACT

Methods for manufacturing baking soda dentifrice compositions containing pyrophosphate tartar control agent using tetrasodium pyrophosphate. The process and compositions have less than about 20% of the pyrophosphate dissolved in the dentifrice composition.

17 Claims, No Drawings

5,456,903

METHOD OF MAKING A TARTAR CONTROL BAKING SODA DENTIFRICE

This is a continuation of application Ser. No. 08/279,305, filed on Jul. 22, 1994, which is a continuation of application Ser. No. 08/052,324, filed on Apr. 23, 1993, both now abandoned.

BACKGROUND OF THE INVENTION

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consists of an inorganic portion which is largely calcium phosphate arranged in a hydroxyapatite crystal lattice structure similar to bone, enamel and dentin. An organic portion is also present and consists of desquamated epithelial cells, leukocytes, salivary sediment, food debris and various types of microorganisms.

As the mature calculus develops, it becomes visibly white or yellowish in color unless stained or discolored by some extraneous agent. This is undesirable from an aesthetic standpoint.

Mechanical removal of calculus periodically by the dentist is routine dental office procedure. A variety of chemical and biological agents have also been suggested to retard calculus formation or to remove calculus after it is formed. Pyrophosphate salts are chemical agents known to have the ability to retard calculus formation as described, for example, in U.S. Pat. No. 4,999,184, to Parran, Jr. et al., issued Mar. 12, 1991, the disclosures of which are incorporated herein by reference in their entirety.

Dentifrice compositions containing pyrophosphate salts and sodium bicarbonate (aka, baking soda) are also known, having been described, for example, in U.S. Pat. No. 5,180,576, to Winston et al., issued Jan. 19, 1993, the disclosures of which are incorporated herein by reference in their entirety. Obtaining stable dentifrice compositions containing sodium bicarbonate and pyrophosphate effective for inhibiting dental calculus formation, however, presents a processing challenge. Pyrophosphate dissolved in these dentifrice compositions is subsequently likely to recrystallize in the form of tetrasodium pyrophosphate decahydrate crystals. These crystals can grow into large, glass-like particles which have negative aesthetics and also have tartar control efficacy concerns.

U.S. Pat. No. 5,180,576 (incorporated hereinbefore) apparently recognizes this problem and describes avoiding it by a manufacturing process whereby the sodium bicarbonate is used to salt out the alkali metal pyrophosphate. The amount of dissolved pyrophosphate salt is therefore said to be relatively low in the final composition and the remaining pyrophosphate particles are said to be undissolved tetrasodium pyrophosphate decahydrate salted out by the sodium bicarbonate. These undissolved pyrophosphate crystals dissolve very quickly, however, when the composition is diluted with water as occurs during use. This then is just another way of practicing the invention disclosed and claimed, for example, in U.S. Pat. No. 4,684,518, to Parran, Jr. et al., issued Aug. 4, 1987, the disclosures of which are incorporated herein by reference in their entirety.

It has been discovered by the present invention that pyrophosphate/sodium bicarbonate-containing dentifrice compositions which are aesthetically acceptable and efficacious may also be prepared by the simpler process of the present invention. The present invention process, unlike the U.S. Patent 5,180,576 process whereby pyrophosphate is dissolved and then salted out, achieves these benefits through controlling the process conditions to insure that less than about 20% of the pyrophosphate is solubilized at any point in the process mixture. Thus, the present invention process provides advantages versus the prior art, such as the U.S. Pat. No. 5,180,576 process, in terms of simplicity of manufacturing by avoiding the need to control crystallization during salting out of the tetrasodium pyrophosphate decahydrate.

Preferably one or more of three processing conditions are controlled while tetrasodium pyrophosphate salt is added to the mixture. These conditions are the temperature of the mixture, and/or the pH of the mixture, and/or the amount of non-pyrophosphate sodium-containing components added to the mixture.

It is therefore an object of the present invention to provide an easily controlled process for preparing a stable dentifrice composition containing sodium bicarbonate and pyrophosphate salts. An object is also to provide stable dentifrice compositions containing sodium bicarbonate and tetrasodium pyrophosphate salt particles of predetermined and/or consistent size. Another object of this invention is to prepare such stable compositions by a process controlling the processing conditions such that less than about 20% of the total pyrophosphate is dissolved in the composition.

These and other objects of the present invention will become readily apparent from the detailed description which follows.

All percentages and ratios used herein are by weight, and all measurements are made at 25° C., unless otherwise specified.

SUMMARY OF THE INVENTION

The present invention relates to a method of manufacturing a baking soda dentifrice composition containing pyrophosphate tartar control agent. Said method comprises the steps of: (a) preparing a mixture of sodium bicarbonate and one or more dentifrice carrier materials; followed by (b) adding tetrasodium pyrophosphate, all at once or in portions, under conditions whereby less than about 20% of the total pyrophosphate is dissolved in the dentifrice mixture; and wherein further any remaining dentifrice carrier materials not added to the mixture during step (a) are added in whole or in part in step (b) or thereafter, either by themselves or with any remaining amount of the tetrasodium pyrophosphate under conditions such that less than about 20% of the total pyrophosphate is dissolved in the mixture; said dentifrice composition manufactured by this process comprising from about 5% to about 50% sodium bicarbonate, from about 10 ppm to about 3500 ppm of fluoride ion from a soluble fluoride ion source, and at least about 1.5% tetrasodium pyrophosphate, with said composition having less than about 20% of the total pyrophosphate dissolved in the dentifrice composition.

The present invention also relates to baking soda dentifrice compositions containing pyrophosphate tartar control agent comprising: (a) from about 5% to about 50% sodium bicarbonate; (b) from about 10 ppm to about 3500 ppm of fluoride ion from a soluble fluoride ion source; (c) at least about 1.5% tetrasodium pyrophosphate, of which some or all of the undissolved tetrasodium pyrophosphate is anhydrous tetrasodium pyrophosphate particles; and (d) from about 50% to about 94% dentifrice carrier materials; and wherein further said composition has less than about 20% of the total pyrophosphate dissolved in the composition.

DETAILED DESCRIPTION OF THE INVENTION

The present invention relates to a method of manufacturing a baking soda dentifrice composition containing pyrophosphate tartar control agent. The dentifrice compositions produced by the present process may be in the form of toothpastes or gels. The term "toothpaste", as used herein, means paste and gel formulations unless otherwise specified. The present invention also relates to such baking soda/pyrophosphate tartar control dentifrice compositions comprising anhydrous tetrasodium pyrophosphate particles.

The present process and compositions comprise several essential components, as well as optional components. A detailed description of these components and the present process conditions are described hereinafter.

A) Tetrasodium Pyrophosphate

The pyrophosphate salt used in the present process and compositions must include tetrasodium pyrophosphate salt. This material may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use.

While tetrasodium pyrophosphate salt particles are a necessary component of the present invention process and compositions, it is to be recognized that low levels of other pyrophosphate salts may be included in the process and compositions. Specific salts include tetra alkali metal pyrophosphate other than tetrasodium pyrophosphate, dialkali metal diacid pyrophosphate, trialkali metal monoacid pyrophosphate and mixtures thereof, wherein the alkali metals are sodium or potassium. [Pyrophosphate salts are described in more detail in Kirk & Othmer, *Encyclopedia of Chemical Technology*, Second Edition, Volume 15, Interscience Publishers (1968), incorporated herein by reference in its entirety.] These salts are useful in both their hydrated and unhydrated forms. Because such salts are typically more soluble than the tetrasodium pyrophosphate salt, their inclusion in the process of the present invention should be limited to avoid preparing compositions containing more than about 20% of the total pyrophosphate dissolved in the composition (preferably less than about 10% of the total pyrophosphate dissolved in the composition), and exclusion of such more soluble salts is preferred.

The amount of tetrasodium pyrophosphate salt useful in these compositions is any tartar control effective amount, and is generally enough to provide at least about 1.0% $P_2O_7^{-4}$, preferably from about 1.5% to about 10%, more preferably from about 3.0% to about 6%, by weight of the compositions. It is to be appreciated that the level of $P_2O_7^{-4}$ is that amount capable of being provided to the composition (i.e., the theoretical amount at an appropriate pH) and that other pyrophosphate forms (e.g., $HP_2O_7^{-3}$) may be present when a final product pH is established. The level of tetrasodium pyrophosphate salt preferably used in the present methods and compositions is therefore from about 1.5% to about 15%, and more preferably from about 2% to about 10%, by weight of the dentifrice composition.

B) Sodium Bicarbonate

Sodium bicarbonate, also known as baking soda, is a household product with a variety of uses including use in dentifrices and mouthrinses. It is a white powder that is soluble in water and unless stabilized, tends to release carbon dioxide in an aqueous system. The present process compositions contain from about 5% to about 50%, preferably from about 10% to about 30%, sodium bicarbonate by weight of the composition.

C) Soluble Fluoride Ion Source

A soluble fluoride ion source is also incorporated in the present process and compositions. The soluble fluoride ion source is used in amounts sufficient to provide from about 10 to about 3500 ppm of the fluoride ion. Preferred fluorides are sodium fluoride, stannous fluoride, indium fluoride, and sodium monofluorophosphate. Norris et al., U.S. Pat. No. 2,946,735, issued Jul. 26, 1960 and Widder et al., U.S. Pat. No. 3,678,154, issued Jul. 18, 1972 disclose such salts as well as others. Both patents are incorporated herein by reference in their entirety.

D) Dentifrice Carrier Materials

In preparing the present toothpaste compositions, it is desirable to add one or more dentifrice carrier materials to the compositions. The term "dentifrice carrier materials", as used herein, means any material safe and effective for use in the toothpaste compositions prepared according to the present invention. Such materials are well known in the art and are readily chosen by one skilled in the art based on the physical and aesthetic properties desired for the dentifrice composition being prepared. Dentifrice carrier materials typically comprise from about 50% to about 94%, preferably from about 60% to about 80%, by weight of the present invention compositions.

The present invention compositions typically contain some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an amount from about 0.2% to about 5% by weight of the total composition.

It is also desirable to include some humectant material in a toothpaste to keep the composition from hardening upon exposure to air. Certain humectants can also impart a desirable sweetness or flavor to toothpaste compositions. Suitable humectants include glycerin, sorbitol, other edible polyhydric alcohols, and mixtures thereof, at a level of from about 15% to about 70%, by weight of the compositions.

Titanium dioxide may also be added to the present compositions. Titanium dioxide is a white powder which adds pigment to the compositions. Titanium dioxide generally comprises from about 0.25% about 1% by weight of the compositions.

Water is also present in the compositions of this process. Water employed in the preparation of commercially suitable toothpastes should preferably be deionized and free of organic impurities. Water generally comprises from about 5% to about 40%, preferably from about 20% to about 35%, by weight of the compositions herein. These amounts of water include the free water which is added plus that which is introduced with other materials such as with sorbitol.

The pH of the present process mixtures and compositions is preferably adjusted through the use of buffering agents. Buffering agents, as used herein, refer to agents that can be used to increase the pH of the process compositions to a range of above about pH 8 as desired for addition of the sodium bicarbonate and tetrasodium pyrophosphate. These agents include trisodium phosphate, sodium hydroxide and sodium carbonate. Sodium carbonate is preferred at a level of from about 0.5% to about 2% by weight of the present compositions.

An abrasive polishing material may also be included. The abrasive polishing material contemplated for use in the compositions of the present process invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used.

Silica dental abrasives of various types are preferred because of their unique benefits of exceptional dental cleaning and polishing performance without unduly abrading tooth enamel or dentin. The silica abrasive polishing materials useful herein, as well as other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, Jun. 21, 1975, both incorporated herein by reference. Preferred are the silica xerogels marketed under the tradename "Syloid" by W. R. Grace & Company, Davison Chemical Division. Preferred precipitated silica materials include those marketed by the J. M. Huber Corporation under the tradename, "Zeodent", particularly the silica carrying the designation "Zeodent 119". These silica abrasives are described in U.S. Pat. No. 4,340,583, Jul. 29, 1982, incorporated herein by reference.

The abrasive in the toothpaste compositions described herein is preferably present at a level of from about 6% to 70%, more preferably from about 10% to about 25%.

The present toothpaste compositions can also contain surfactants. Suitable surfactants are those which are reasonably stable and foam throughout a wide pH range, including non-soap anionic, nonionic, cationic, zwitterionic and amphoteric organic synthetic detergents. Many of these suitable agents are disclosed by Gieske et al. in U.S. Pat. No. 4,051,234, Sep. 27, 1977, incorporated herein by reference. Sodium alkyl sulfate and polyethylene glycol are preferred for use in the present process and compositions at a level of from about 0.5% to about 5% by weight of the compositions.

Flavoring agents can also be added to the present compositions. Suitable flavoring agents include oil of wintergreen, oil of peppermint, oil of spearmint, oil of sassafras, and oil of clove. Sweetening agents which can be used include aspartame, acesulfame, saccharin, dextrose, levulose and sodium cyclamate. Flavoring and sweetening agents are generally used in toothpastes at levels of from about 0.005% to about 2% by weight of the composition.

The present invention compositions may also contain optional pharmaceutical agents (e.g., triclosan) and other tartar control agents. Optional tartar control agents include such known materials as synthetic anionic polymers [including polyacrylates and copolymers of maleic anhydride or acid and methyl vinyl ether (e.g., Gantrez), as described for example in U.S. Pat. No. 4,627,977 to Gaffar et al., the disclosures of which are incorporated herein by reference in their entirety; as well as, e.g., polyamino propane sulfonic acid (AMPS)], polyphosphates (e.g., tripolyphosphate; hexametaphosphate), diphosphonates (e.g., EHDP; AHP), polypeptides (such as polyaspartic and polyglutamic acids), and mixtures thereof.

Method of Manufacturing

Toothpaste compositions of the present process invention are prepared by mixing together the components described above according to the method of manufacturing of the present invention. This method comprises the steps of: (a) preparing a mixture of sodium bicarbonate and one or more dentifrice carrier materials; followed by (b) adding tetrasodium pyrophosphate, all at once or in portions, under conditions whereby less than about 20% of the total pyrophosphate is dissolved in the dentifrice mixture; and wherein further any remaining dentifrice carrier materials not added to the mixture during step (a) are added in whole or in part in step (b) or thereafter, either by themselves or with any remaining amount of the tetrasodium pyrophosphate, under conditions such that less than about 20% of the total pyrophosphate is dissolved in the mixture. Preferably, the amount of pyrophosphate dissolved in the mixture for the methods and compositions of the present invention is less than about 10% by weight of the total pyrophosphate present in the compositions. A method for measuring the amount of pyrophosphate dissolved in the mixture and compositions is described and exemplified hereinafter in the Examples.

Preferably, one or more of the following process conditions are controlled as follows to limit the solubility of the tetrasodium pyrophosphate in the dentifrice mixture: (1) the neat (undiluted) pH of the process mixture is above about pH 8 during and after the tetrasodium pyrophosphate is added to the mixture; (2) the tetrasodium pyrophosphate salt is one of the last components to be added to the process mixture, preferably after all or much of the other sodium-containing salts present in the composition have been added to the process mixture; and (3) during and after the tetrasodium pyrophosphate salt is added, the temperature of the mixture is not greater than about 140° F. (60° C.), and preferably during addition is less than about 100° F. (38° C.).

The following examples further describe and demonstrate embodiments within the scope of the present invention. These examples are given solely for the purpose of illustration and are not to be construed as limitations of the present invention as many variations thereof are possible without departing from the spirit and scope.

EXAMPLES

| Ingredient | 3.3% $P_2O_7^{-4}$ Paste | 3.3% $P_2O_7^{-4}$ Gel | 5.0% $P_2O_7^{-4}$ Paste | 5.0% $P_2O_7^{-4}$ Gel |
| --- | --- | --- | --- | --- |
| Sodium bicarbonate | 20.000 | 20.000 | 17.000 | 17.000 |
| Water | 19.723 | 19.723 | 20.334 | 20.334 |
| Silica | 18.000 | 18.000 | 16.000 | 16.000 |
| Glycerin | 15.000 | 15.000 | 19.000 | 19.000 |
| Sorbitol (70%) | 11.161 | 11.211 | 8.951 | 9.001 |
| Tetrasodium pyrophosphate | 5.045 | 5.045 | 7.644 | 7.644 |
| Sodium alkyl sulfate (27.9%) | 4.000 | 4.000 | 4.000 | 4.000 |
| PEG-6 | 3.000 | 3.000 | 3.000 | 3.000 |
| Sodium carbonate | 1.250 | 1.250 | 1.250 | 1.250 |
| Flavor | 1.000 | 1.000 | 1.000 | 1.000 |
| Carboxymethylcellulose | 0.700 | 0.700 | 0.700 | 0.700 |
| Sodium saccharin | 0.528 | 0.528 | 0.528 | 0.528 |
| Titanium dioxide | 0.350 | — | 0.350 | — |
| Sodium fluoride | 0.243 | 0.243 | 0.243 | 0.243 |
| FD & C Blue No. 1 | — | 0.300 | — | 0.300 |
| | 100.000 | 100.000 | 100.000 | 100.000 |

The paste compositions are prepared as follows by a method encompassed by the present invention. To the water is added the sorbitol, sodium fluoride, sodium saccharin, part of the flavor, sodium carbonate, titanium dioxide, carboxymethylcellulose and glycerine, and silica. To this mixture is then added the sodium bicarbonate, followed by the remainder of the flavor and sodium alkyl sulfate. To this mixture at about 95° F. (35° C.) is then added the tetrasodium pyrophosphate, glycerine and PEG-6 to provide the final paste product. Gel compositions are manufactured by a similar process.

Measurement of the level of soluble pyrophosphate in these compositions is accomplished as follows. The whole dentifrice composition is centrifuged at 28,000 rpm for two hours. The resulting two liquid layers are then removed from the solid plug and mixed together thoroughly for analysis by ion chromatography. The soluble pyrophosphate present in the 3.3% $P_2O_7^{-4}$ paste, for example, is thereby determined to be 0.16% (by weight of the paste composition), which is 4.8% of the total pyrophosphate present in the composition.

What is claimed is:

1. A method of manufacturing a baking soda aqueous paste or gel dentifrice composition containing pyrophosphate tartar control agent; said method comprising the steps of:

(a) preparing a mixture of sodium bicarbonate and one or more dentifrice carrier materials; followed by (b) adding tetrasodium pyrophosphate, all at once or in portions, under conditions whereby less than about 20% of the total pyrophosphate is dissolved in the dentifrice mixture; and wherein any further remaining dentifrice carrier materials not added to the mixture during step (a) are added in whole or in part in step (b) or thereafter, either by themselves or with any remaining amount of the tetrasodium pyrophosphate under conditions such that less than about 20% of the total pyrophosphate is dissolved in the mixture;

said dentifrice composition manufactured by this process comprising from about 10% to about 50% sodium bicarbonate, from about 50% to about 94% carrier materials, from about 10 ppm to about 3500 ppm of fluoride ion from a soluble fluoride ion source, and at least about 1.5% tetrasodium pyrophosphate, with said composition having less than about 20% of the total pyrophosphate dissolved in the dentifrice composition, wherein said dentifrice composition containing dissolved tetrasodium pyrophosphate salt being less likely to recrystallize in the form of glass-like crystal particles of tetrasodium pyrophosphate decahydrate.

2. The method of manufacturing a baking soda dentifrice composition containing pyrophosphate tartar control agent according to claim 1 wherein the pH of the mixture is above about pH 8 during and after the tetrasodium pyrophosphate is added to the mixture.

3. The method of manufacturing a baking soda dentifrice composition containing pyrophosphate tartar control agent according to claim 1 wherein the tetrasodium pyrophosphate is added to the mixture after all the other sodium-containing salts present in the composition have been added to the mixture.

4. The method of manufacturing a baking soda dentifrice composition containing pyrophosphate tartar control agent according to claim 1 wherein the temperature of the mixture during and after the tetrasodium pyrophosphate salt is added is not greater than about 140° F.

5. The method of manufacturing a baking soda dentifrice composition containing pyrophosphate tartar control agent according to claim 1 wherein the composition further comprises a buffering agent selected from the group consisting of trisodium phosphate, sodium hydroxide, sodium carbonate, and mixtures thereof.

6. The method of manufacturing a baking soda dentifrice composition containing pyrophosphate tartar control agent according to claim 1 wherein the soluble fluoride ion source is selected from the group consisting of sodium fluoride, stannous fluoride, indium fluoride and sodium monofluorophosphate.

7. The method of manufacturing a baking soda dentifrice composition containing pyrophosphate tartar control agent according to claim 1 wherein the dentifrice carrier material is selected from the group consisting of surfactants, abrasive polishing materials, sweetening agents, flavoring agents, coloring agents, titanium dioxide, water, and mixtures thereof.

8. A method of manufacturing a baking soda aqueous paste or gel dentifrice composition containing pyrophosphate tartar control agent, said method comprising the steps of:

(a) creating a mixture of dentifrice carrier materials selected from the group consisting of thickening agents, humectants, water, buffering agents, abrasive polishing materials, water soluble fluoride ion sources, surfactants, sweetening agents, flavoring agents, titanium dioxide, and mixtures thereof having a pH above about pH 8;

(b) adding sodium bicarbonate to the mixture; and then (c) adding tetrasodium pyrophosphate, all at once or in portions, under conditions whereby less than about 20% of the; total pyrophosphate is dissolved in the dentifrice mixture; and wherein further any remaining dentifrice carrier materials not added to the mixture during steps (a) or (b) are added in whole or in part in step (c) or thereafter, either by themselves or with any remaining amount of the tetrasodium pyrophosphate under conditions such that less than about 20% of the total pyrophosphate is dissolved in the mixture;

said dentifrice composition manufactured by this process comprising from about 10% to about 50% sodium bicarbonate, from about 50% to about 94% carrier materials, from about 10 ppm to about 3500 ppm of fluoride ion from a soluble fluoride ion source, and at least about 1.5% tetrasodium pyrophosphate, with said composition having less than about 20% of the total pyrophosphate dissolved in the dentifrice composition, wherein said dentifrice composition containing dissolved tetrasodium pyrophosphate salt being less likely to recrystallize in the form of glass-like crystal particles of tetrasodium pyrophosphate decahydrate.

9. The method of manufacturing a baking soda dentifrice composition containing pyrophosphate tartar control agent according to claim 8 wherein the pH of the mixture is above about pH 8 during and after the tetrasodium pyrophosphate is added to the mixture.

10. The method of manufacturing a baking soda dentifrice composition containing pyrophosphate tartar control agent according to claim 8 wherein the tetrasodium pyrophosphate is added to the mixture after all the other sodium-containing salts present in the composition have been added to the mixture.

11. The method of manufacturing a baking soda dentifrice composition containing pyrophosphate tartar control agent according to claim 8 wherein the temperature of the mixture during and after the tetrasodium pyrophosphate salt is added is not greater than about 140° F.

12. The method of manufacturing a baking soda dentifrice composition containing pyrophosphate tartar control agent according to claim 8 further comprising a buffering agent selected from the group consisting of trisodium phosphate, sodium hydroxide, sodium carbonate, and mixtures thereof.

13. A method of manufacturing a baking soda aqueous paste or gel dentifrice composition containing pyrophosphate tartar control agent, said method comprising the steps of:

(a) creating a mixture of dentifrice carrier materials selected from the group consisting of thickening agents, humectants, water, buffering agents, abrasive polishing materials, water soluble fluoride ion sources, surfactants, sweetening agents, flavoring agents, titanium dioxide, and mixtures thereof having a pH above about pH 8;

(b) adding sodium bicarbonate to the mixture; and then (c) adding tetrasodium pyrophosphate, all at once or in portions, under conditions of a temperature less than about 100° F. and at a pH above about pH 8 whereby less than about 10% of the total pyrophosphate is dissolved in the dentifrice mixture; and wherein further any remaining dentifrice carrier materials not added to the mixture during steps (a) or (b) are added in whole or in part in step (c) or thereafter, either by themselves or with any remaining amount of the tetrasodium pyrophosphate under conditions of a temperature less than about 100° F. and at a pH above about pH 8 such that less than about 10% of the total pyrophosphate is dissolved in the mixture;

said dentifrice composition manufactured by this process comprising from about 10% to about 50% sodium bicarbonate, from about 50% to about 94% carrier materials, from about 10 ppm to about 3500 ppm of fluoride ion from a soluble fluoride ion source, and at least about 1.5% tetrasodium pyrophosphate, with said composition having less than about 10% of the total pyrophosphate dissolved in the dentifrice composition, wherein said dentifrice composition containing dissolved tetrasodium pyrophosphate salt being less likely to recrystallize in the form of glass-like crystal particles of tetrasodium pyrophosphate decahydrate.

14. The method of manufacturing a baking soda dentifrice composition containing pyrophosphate tartar control agent according to claim 13 wherein the tetrasodium pyrophosphate is added to the mixture after all the other sodium-containing salts present in the composition have been added to the mixture.

15. The method of manufacturing a baking soda dentifrice composition containing pyrophosphate tartar control agent according to claim 14 wherein sodium carbonate buffering agent is added to the composition.

16. The method of manufacturing a baking soda dentifrice composition containing pyrophosphate tartar control agent according to claim 8 wherein the soluble fluoride ion source is selected from the group consisting of sodium fluoride, stannous fluoride, indium fluoride and sodium monofluorophosphate.

17. The method of manufacturing a baking soda dentifrice composition containing pyrophosphate tartar control agent according to claim 13 wherein the soluble fluoride ion source is selected from the group consisting of sodium fluoride, stannous fluoride, indium fluoride and sodium monofluorophosphate.

* * * * *